(12) United States Patent
Han et al.

(10) Patent No.: US 8,507,275 B2
(45) Date of Patent: Aug. 13, 2013

(54) METHOD OF INDUCING DIFFERENTIATION OF EMBRYONIC STEM CELLS INTO HEMANGIOBLAST

(75) Inventors: Yong-Mahn Han, Daejeon (KR); Sang-Wook Park, Busan (KR); Eun-Young Lee, Daejeon (KR)

(73) Assignee: Korea Advanced Institute of Science and Technology (Kaist), Daejeon (KR)

( * ) Notice: Subject to any disclaimer, the term of this patent is extended or adjusted under 35 U.S.C. 154(b) by 342 days.

(21) Appl. No.: 12/858,747

(22) Filed: Aug. 18, 2010

(65) Prior Publication Data

US 2011/0027886 A1 Feb. 3, 2011

Related U.S. Application Data

(63) Continuation of application No. PCT/KR2008/000952, filed on Feb. 18, 2008.

(51) Int. Cl.
*C12N 5/00* (2006.01)
*C12N 5/02* (2006.01)
*C12N 5/08* (2006.01)
*A01N 61/00* (2006.01)
*A01N 37/18* (2006.01)

(52) U.S. Cl.
USPC ............ 435/377; 435/366; 514/1; 514/2

(58) Field of Classification Search
USPC .................. 435/366, 377; 514/1, 2
See application file for complete search history.

(56) References Cited

U.S. PATENT DOCUMENTS

| 2003/0153082 A1 | 8/2003 | Bhatia |
| 2004/0214319 A1 | 10/2004 | Pebay et al. |
| 2007/0178439 A1* | 8/2007 | Smith et al. |
| 2008/0108044 A1* | 5/2008 | Rajesh et al. |

FOREIGN PATENT DOCUMENTS

| KR | 10-2006-0016133 A | 2/2006 |
| KR | 10-2006-0058476 A | 5/2006 |
| WO | WO 03/040319 A2 | 5/2003 |

OTHER PUBLICATIONS

Zhang et al., 2008, Blood, vol. 111, No. 4, p. 1933-1941.*
Wiles et al., 1999, Experimental Cell Research, vol. 247, p. 241-248.*
Allegrucci et al., 2006, Human Reproduction Update, Vol. Advance Access published on Aug. 26, 2006, p. 1-18.*
Sato et al., 2003, Developmental Biology, vol. 260, p. 404-413.*
Abeyta et al., 2004, Human Molecular Genetics, vol. 13, No. 6, p. 601-608.*
Kolf et al., 2007, Arthritis Research & Therapy, vol. 9, p. 204, 10 pages.*
Alenzi et al., 2011, African Journal of Biotechnology, vol. 10(86), pp. 19929-19940.*
Skolnick et al., 2000, Trends in Biotech, vol. 18, p. 34-39.*
Tomasinsig et al., 2005, Current Protein and Peptide Science, vol. 6, p. 23-34.*
Smallwood et al., 2002 Virology, vol. 304, p. 135-145.*
Chattopadhyay et al., 2004, Virus Research, vol. 99, p. 139-145.*
Kennedy et al., 2007, Blood, vol. 109, No. 7, p. 2679-2687.*
Burdon, T. et al., Signaling, cell cycle and pluripotency in embryonic stem cells, Trends in Cell Biology, Sep. 2002, vol. 12, Issue 9, pp. 432-438.
Enarsson, M. et al., Extracellular signal-regulated protein kinases signaling is uncoupled from initial differentiation of central nervous system stem cells to neurons, Molecular Cancer Research, Dec. 2002, vol. 1, pp. 147-154.
Gerecht-Nir, S. et al., Cell therapy using human embryonic stem cells, Transplant Immunology, 2004, vol. 12, pp. 203-209.
Hori, Y. et al., Growth inhibitors promote differentiation of insulin-producing tissue from embryonic stea cells, Proc. Nat'l. Acad. Sci. USA, Dec. 10, 2002, vol. 99, Issue 25, pp. 16105-16110.
International Search Report issued for PCT/KR2008/000952 dated Oct. 22, 2008.
Itskovitlz-Eldor, J. et al., Differentiation of human embryonic stem cells into embryoid bodies comprising the three embryonic germ layers, Molecular Medicine, 2000, vol. 6(2), pp. 88-95.
Kim, J.H. et al., Dopamine neurons derived from embryonic stem cells function in an animal model of Parkinson's disease, Nature, Jul. 4, 2002, vol. 418, pp. 50-56.
Minguell, J. et al., Mesenchymal stem cells, Exp. Biol. Med., 2001, vol. 226, pp. 507-520.
O'Shea, K.S. et al., Embryonic stem cell models of development, The Anatomical Record (New Anat.), 1999, vol. 257, pp. 32-41.
Schuldiner, M. et al., Effects of eight growth factors on the differentiation of cells derived from human embryonic stem cells, Proc. Nat'l Acad. Sci., Oct. 10, 2000, vol. 97, Issue 21, pp. 11307-11312.

(Continued)

*Primary Examiner* — Shin-Lin Chen
(74) *Attorney, Agent, or Firm* — Knobbe, Martens, Olson & Bear, LLP

(57) ABSTRACT

The present invention relates to a composition for inducing embryonic stem cell differentiation comprising a MEK/ERK (mitogen-activated protein kinase kinase/extracellular regulated kinase) signal transduction inhibitor and BMP (bone morphogenetic protein), and a method for inducing differentiation of embryonic stem cells into mesodermal cells using the same. Further, the mesodermal cells obtained by the above method are able to differentiate into various mesenchymal tissue cells. In particular, the present invention relates to a method for inducing differentiation into hemangioblast by culturing the mesodermal cells obtained by the above method in the presence of VEGF (vascular endothelial cell growth factor) and bFGF (basic fibroblast growth factor). The differentiated hemangioblasts can be further differentiated into vascular endothelial cells, vascular smooth muscle cells, and hematopoietic stem cells under various culture conditions.

7 Claims, 6 Drawing Sheets

(56) References Cited

OTHER PUBLICATIONS

Thomson, J.A. et al., Embryonic stem cell lines derived from human blastocysts, Science, Nov. 6, 1998, vol. 282, pp. 1145-1147.

Vodyanik, M.A. et al., Human embryonic stem cell-derived CD34 cells: efficient production in the coculture with OP9 stromal cells and analysis of lymphohematopoietic potential, Blood, Jan. 15, 2005, vol. 105, Issue 2, pp. 617-626.

Wang, Z. et al., Endothelial cells derived from human embryonic stem cells form durable blood vessels in vivo, Nature Biotechnology, Mar. 2007, vol. 25, Issue 3, pp. 317-318.

Wobus, A.M. et al., Preface, Cells Tissues Organs, 1999, vol. 165, pp. 129-130.

* cited by examiner (a)

(b) PECAM-1

(c) vWF (d) VE-cadherin (e) AcLDL-uptake (f) Morphology (g) Matrigel assay

Macrophage

BFU-E

CFU-E

CFU-G

METHOD OF INDUCING DIFFERENTIATION OF EMBRYONIC STEM CELLS INTO HEMANGIOBLAST

CROSS-REFERENCE TO RELATED PATENT APPLICATION

This application is a continuation application under 35 U.S.C. §365(c) of International Application No. PCT/KR2008/000952, filed Feb. 18, 2008 designating the United States. This application incorporates herein by reference the International Application No. PCT/KR2008/000952 in their entirety.

TECHNICAL FIELD

The present invention relates to a composition for inducing stem cell differentiation comprising a MEK/ERK signal transduction inhibitor and BMP, and a method for inducing differentiation of embryonic stem cells into mesodermal cells using the same. Further, the mesodermal cells obtained by the above method are able to differentiate into various mesenchymal tissue cells. In particular, the present invention relates to a method for inducing differentiation into hemangioblasts by culturing the mesodermal cells obtained by the above method in the presence of VEGF (vascular endothelial cell growth factor) and bFGF (basic fibroblast growth factor). The differentiated hemangioblasts can be further differentiated into vascular endothelial cells, vascular smooth muscle cells, and hematopoietic stem cells under various culture conditions.

BACKGROUND

Human embryonic stem cells (hESCs) are stem cells derived from the inner cell mass of blastocysts (J. A. Thomson et al, Science 282, 1145-1147, 1998), and exhibit the properties of self-renewal capacity and pluripotency, which is the ability to differentiate into a wide variety of cell types in the human body (K. S. O'Shea et al, Anat Rec 257, 32-41, 1999; A. M. Wobus et al, Preface, Cells Tissues Organs 165, 129-130, 1999). It has been known that these properties of human embryonic stem cells lead to potential applications in the treatment of diseases that result from the destruction or dysfunction of specific cell types, such as diabetes and Parkinson's disease (J. H. Kim et al. Nature 418, 50-56, 2002; S. Gerecht-Niretal, Transpl Immunol 12, 203-209, 2004; Y. Hori et al, Proc Natl Acad Sci USA 99, 16105-16110, 2002). To date, many research groups have made studies on the differentiation of human embryonic stem cells into diverse cell types. There are three general methods for the differentiation of human embryonic stem cells: First, human embryonic stem cells are differentiated into embryoid bodies (Itskovitz-Eldor J et al. Mol Med 6:88-95, 2000). Second, human embryonic stem cells are cultured as a monolayer in the presence of animal serum such as FBS or FCS for spontaneous differentiation (Wang et al. Nature biotech 25, 317-318, 2007). Third, human embryonic stem cells are co-cultured with other differentiated cells (Vodyanik, M. A. et al. Blood 105, 617-626, 2005). In the above differentiation methods, it is adopted that conditions for spontaneous differentiation of human embryonic stem cells are optimized to induce generation of diverse cell types, and the desired cell types are isolated from the diverse differentiated cells. Thus, there are problems in that the efficiency of differentiation into specific cell types is low, and in particular, any use of animal-derived components or sera in culture systems for human embryonic stem cells should be avoided for the research on early human development.

On the other hand, embryonic stem cells are able to differentiate into the ectodermal, mesodermal, and endodermal lineages. Of these, the multipotent stem cells of mesodermal origin during development give rise to the bone, cartilage, tendon, muscle, adipose tissue and vascular endothelium (Minguell et al., Esp. Biol. Med. 226, 507-520, 2001). The hemangioblast would represent a cell population developing from uncommitted mesoderm. Since the mesenchymal stem cells retain a self-renewing property, implantation of these cells in various animal model systems leads to the differentiation of these cells at localized sites and the subsequent regeneration of tissues such as blood vessels and various blood cells. Thus, the mesenchymal stem cells can be used for cell therapy. To yield a sufficient amount of the mesenchymal stem cells for use in cell therapy, a technique to induce the differentiation of embryonic stem cells into mesenchymal stem cells is needed. However, to date, there are no reports on the method of effectively inducing the differentiation of embryonic stem cells into mesenchymal stem cells.

In addition, techniques to induce differentiation of embryonic stem cells into hemangioblasts are as follows: a method of inducing the direct differentiation of embryonic stem cells into endothelial cells by culturing the embryonic stem cells in a medium containing VEGF, bFGF, IGF (insulin-like growth factor) and EGF (epidermal growth factor) (WO 03/040319), a method for generating hematopoietic lineage by culturing embryonic stem cells in a medium containing hematopoietic growth factors selected from SCF (stem cell factor), FLT-3 ligand, IL-3, IL-6 and G-CSF (granulocyte colony stimulating factor) (US Patent publication No. US 2003/0153082), a method for inducing differentiation of human embryoid bodies into hemopoietic stem cells by co-culturing human embryoid bodies with human placenta stromal cells (Korean Patent Application No. 10-2006-0009934), and a method for promoting differentiation of human embryoid bodies to hemopoietic stem cells by co-culturing human embryoid bodies with human bone marrow stromal cells (Korean Patent Application No. 10-2004-0097538). However, there are still no trials that induce differentiation into hemangioblast by regulating the embryonic stem cell signaling pathway.

SUMMARY

Accordingly, the present inventors have conducted extensive research on methods for more effectively inducing differentiation of embryonic stem cells into mesenchymal stem cells by regulating the embryonic stem cell signaling pathway, and as a result, discovered that treatment of embryonic stem cells with a MEK/ERK signal transduction inhibitor and BMP can induce high efficiency of differentiation into mesenchymal stem cells, and moreover, exhibits the most prominent effect on differentiation into hemangioblast by treatment of the mesenchymal stem cells with VEGF and bFGF. Such methods are advantageous in that a variety of cells can be effectively generated by regulation of the signaling pathway in human embryonic stem cells without any addition of animal serum.

It is an aspect of the present invention to provide a composition for inducing embryonic stem cell differentiation, comprising a MEK/ERK signal transduction inhibitor and BMP.

It is another aspect of the present invention to provide a method for inducing differentiation of embryonic stem cells into mesodermal cells using the composition.

It is still another aspect of the present invention to provide a method for inducing differentiation into hemangioblasts by culturing the mesodermal cells obtained by the above method in the presence of VEGF and bFGF.

It is still another aspect of the present invention to provide a method for inducing differentiation into vascular endothelial cells by culturing the hemangioblasts obtained by the above method in the presence of VEGF and bFGF.

It is still another aspect of the present invention to provide a method for inducing differentiation into vascular smooth muscle cells by culturing the hemangioblasts obtained by the above method in the presence of PDGF-BB.

It is still another aspect of the present invention to provide a method for inducing differentiation into hematopoietic stem cells by culturing the hemangioblasts obtained by the above method in MethCult GF H4434 (Stem Cell Technologies, Canada).

DETAILED DESCRIPTION OF THE EMBODIMENTS

Figure 1:
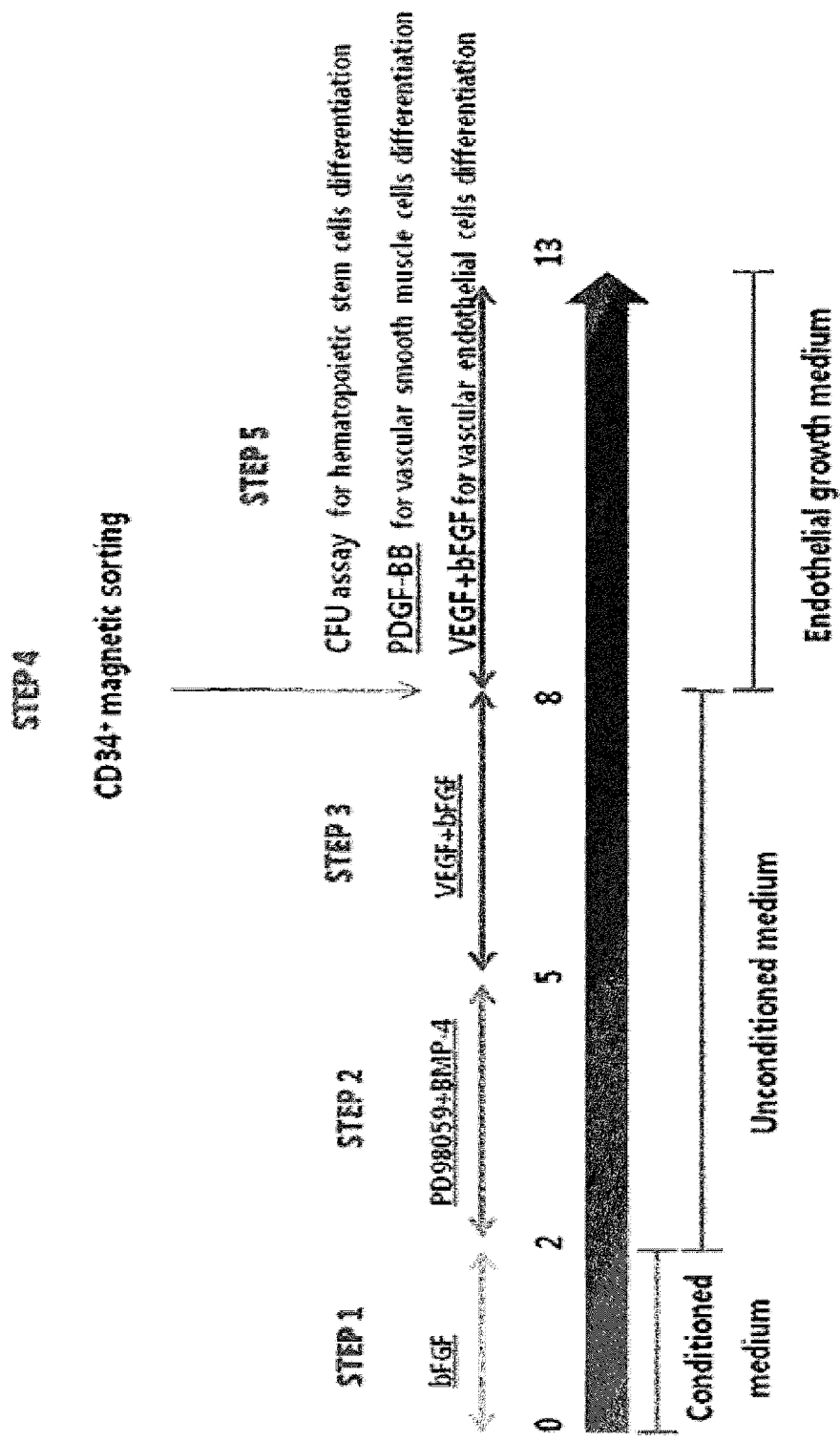
FIG. 1 is a diagram illustrating a method for inducing the differentiation of human embryonic stem cells into hemangioblasts, which further differentiate into hematopoietic stem cells, vascular endothelial cells, and vascular smooth muscle cells.

Accordingly, in accordance with an aspect, the present invention relates to a composition for inducing embryonic stem cell differentiation, comprising a MEK/ERK signal transduction inhibitor and BMP.

The term "embryonic stem cells", as used herein, refers to pluripotent or totipotent cells capable of differentiating into any type of cell, derived from the inner cell mass of blastocysts at a stage before it would implant in the uterine wall, and embraces embryoid bodies derived from embryonic stem cells. Embryoid bodies are the intermediate structures formed by stem cells in the process of spontaneous differentiation into a variety of tissue types, and in the form of cell aggregates formed during culture of embryonic stem cells. On the other hand, the embryonic stem cells of some embodiments of the present invention may be derived from mammals including human, preferably human embryonic stem cells.

The term "differentiation", as used herein, refers to a phenomenon in which the structure or function of cells is specialized during the division, proliferation and growth thereof. Pluripotent embryonic stem cells give rise to progenitor cells that gradually differentiate into committed cell lineages (e.g., ectodermal, mesodermal, and endodermal cells, etc.), and may further differentiate into other types of progenitor cells (e.g., hemangioblast, etc.), which in turn generate terminally differentiated cell types (e.g., vascular endothelial cells and vascular smooth muscle cells, etc.) that have specialized functions in the specialized tissues (e.g., blood vessels, etc.).

The term "MEK/ERK signal transduction inhibitor", as used herein, refers to substances targeting ERK1/2 and its upstream kinase MEK1/2, involved in MEK/ERK (mitogen-activated protein kinase kinase/extracellular regulated kinase) signal transduction pathway.

MEK (mitogen-activated protein kinase kinase) is an enzyme that acts on MAP kinase cascade in the cytoplasm and functions as an important mediator of extracellular signals, and is responsible for in vitro phosphorylation of threonine (Thr) residue in myelin basic protein. ERK is a representative MAP kinase present in higher organisms, and phosphorylates threonine (Thr) and tyrosine (Tyr) residues in response to extracellular signals. It has been reported that such phosphorylation of threonine and tyrosine residues plays an important role in activation of MAP kinase, and thus substitution of other amino acids for these amino acid residues results in enzyme inactivation.

Some aspects of the present invention demonstrate, for the first time, that an inhibition of the MEK/ERK signal transduction pathway is sufficient to regulate stem cell differentiation, and the MEK/ERK signal transduction inhibitor included in the composition according to some embodiments of the present invention is preferably PD98059 or U0126. PD98059 is represented by 2-(2-amino-3-methoxyphenyl)-4H-1-Benzopyran-4-one2-(2'-Amino-3'-methoxy)-flavone2-(2-amino-3-methoxyphenyl)-chromone, and U0126 is represented by 1,4-diamino-2,3-dicyano-1,4-bis[2-aminophenylthio]butadiene. However, it will be apparent to those skilled in the art that all other MEK/ERK signal transduction inhibitors are also included within the scope of some embodiments of the present invention. ERK1/2 is activated by MEK 1/2, and inhibition of MEK1/2 activity immediately inhibits ERK1/2 activity, indicating that MEK1/2 is the immediate upstream activator of ERK1/2.

The term "BMP (bone morphogenetic protein)", as used herein, refers to one or more of growth factors known for their ability to induce the formation of bone, but is used herein as a substance to regulate the differentiation of embryonic stem cells. BMP according to some embodiments of the present invention is preferably BMP-2, BMP-4, or BMP-7.

Some embodiments of the present invention are characterized in that embryonic stem cells are cultured under stimulation with the MEK/ERK signal transduction inhibitor and BMP. The stimulation method is not particularly limited, but preferably exemplified by addition of the above substances to culture media. In addition, any method can be employed, as long as it exhibits the same effect as addition of the above substances to culture media.

The composition according to some embodiments of the present invention may include only the MEK/ERK signal transduction inhibitor and BMP as an inducer for stem cell differentiation, or additionally other differentiation inducers to generate a synergistic effect between the differentiation inducers. Any known inducers for stem cell differentiation may be additionally used as the differentiation inducer that is included in the composition according to some embodiments of the present invention. In regard to the composition according to some of certain embodiments of the present invention, the MEK/ERK signal transduction inhibitor is preferably contained in a medium composition at a concentration of 20 μM to 50 μM, and BMP is preferably contained in a medium composition at a concentration of 10 μM to 20 μM.

In addition, when the composition in some other embodiments of the present invention is used in the form of medium composition, it may contain general media supplements, for example, serum, amino acids, antibiotics, and differentiation regulators, but is not limited thereto.

The composition for inducing embryonic stem cell differentiation comprising a MEK/ERK signal transduction inhibitor and BMP according to some embodiments of the present invention is able to effectively induce the differentiation of embryonic stem cells into mesodermal lineage cells including mesodermal cells. Examples of the mesodermal lineage cells include mesodermal cells, hemangioblast, vascular endothelial cells, vascular smooth muscle cells, and hematopoietic stem cells.

The term "mesodermal cell", as used herein, refers to a multipotent stem cell of mesodermal origin, and gives rise to the bone, cartilage, tendon, muscle, adipose tissue and vascular endothelium during development (Minguell et al., Esp. Biol. Med. 226, 507-520, 2001). The hemangioblast would represent a cell population developing from uncommitted mesoderm. The mesodermal cell of some embodiments of the present invention has the properties of self-renewal capacity and pluripotency.

In order to confirm the differentiation of embryonic stem cells into mesodermal cells, mesoderm-specific markers may be used. Examples of the mesoderm-specific markers may include Goosecoid, Brachyury, TBX-4, TBX-5, and TBX-6. A method for detecting expression of the mesoderm-specific markers is not particularly limited, but may include any molecular biological techniques that are generally used to amplify, detect, or translate mRNA encoding any marker protein by Reverse Transcriptase-Polymerase Chain Reaction (RT-PCR) or hybridization analysis. The nucleic acid sequences encoding the mesoderm-specific markers have been already disclosed, and available in the public database such as GenBank, thereby readily determining the marker specific sequences to be used as a primer or probe. More preferably, the marker expression can be measured at protein level using an immunochemical method such as immunohistochemical staining method and immunoelectrophoresis. In the immunochemical method, polyclonal antibodies or monoclonal antibodies that are specific to the markers binding to mesodermal cells can be used, and commercially available antibodies may be used.

In addition, the composition according to some embodiments of the present invention may further comprise VEGF and bFGF, which can induce differentiation of mesodermal cells into hemangioblasts.

In accordance with another aspect, the present invention relates to a method for inducing the differentiation of embryonic stem cells into mesodermal cells using the composition for inducing embryonic stem cell differentiation comprising a MEK/ERK signal transduction inhibitor and BMP.

Further, the present invention relates to a method for inducing the differentiation into hemangioblasts by culturing the mesodermal cells obtained by the above method in the presence of VEGF and bFGF. Further, the present invention relates to a method for inducing the differentiation into vascular endothelial cells by culturing the hemangioblasts obtained by the above method in the presence of VEGF and bFGF. Further, the present invention relates to a method for inducing the differentiation into vascular smooth muscle cells by culturing the hemangioblasts obtained by the above method in the presence of PDGF-BB. Furthermore, the present invention relates to a method for inducing the differentiation into hematopoietic stem cells by culturing the hemangioblasts obtained by the above method in MethCult GF H4434 medium.

Specifically, the method for inducing embryonic stem cell differentiation according to some embodiments of the present invention may comprise the steps of 1) preparing undifferentiated embryonic stem cells; 2) culturing the embryonic stem cells in a medium that contains a composition for inducing embryonic stem cell differentiation comprising a MEK/ERK signal transduction inhibitor and BMP, so as to differentiate into mesodermal cells; 3) culturing the differentiated mesodermal cells in the presence of VEGF and bFGF, so as to differentiate into hemangioblasts; and 4) differentiating the differentiated hemangioblasts into vascular endothelial cells, vascular smooth muscle cells, and hematopoietic stem cells.

First, step 1) is a step for preparing undifferentiated embryonic stem cells, in which embryonic stem cells are preferably co-cultured with feeder cells. In general, serum is used for cell proliferation. However, since embryonic stem cells cannot be maintained in an undifferentiated state in the presence of serum, they are co-cultured on feeder cells, instead of serum. As the feeder cell, mitomycin C-treated mouse embryonic fibroblast (MEF) or STO (ATCC, USA) may be used.

In feeder-free culture, embryonic stem cells may be cultured on matrigel-coated culture plate in a medium conditioned by feeder cells (CM). The term "conditioned medium", as used herein, refers to a medium that is obtained by culturing the feeder cell, MEF or STO in human embryonic stem cell medium supplemented with bFGF. Specifically, in some embodiments of the present invention, in order to prepare the conditioned medium, STO (ATCC, USA) was used as the feeder cell, and cultured in DMEM (Invitrogen, USA) medium supplemented with 10% fetal bovine serum (Hyclone, USA), 0.1 mM non-essential amino acids, 1× penicillin/streptomycin, and 0.5 mM beta-merchaptoethanol, followed by inactivation in 10 μg/ml mitomycin-C (Sigma, USA) for 2 hrs and 30 min.

Step 2) is a step for inducing the differentiation into mesodermal cells by treating the embryonic stem cell-derived embryoid bodies with the MEK/ERK signal transduction inhibitor and BMP. Any inhibitor may be used without limitation, as long as it inhibits MEK/ERK signal transduction to prevent normal functioning of the signaling pathway. Preferably, PD98059 or U0126 may be used. At this time, the MEK/ERK signal transduction inhibitor is preferably contained in the culture medium at a concentration of 20 to 50 μM. The BMP is preferably BMP-2, 4 or 7, and contained in the culture medium at a concentration of 10 to 20 μM. It is preferable that the MEK/ERK signal transduction inhibitor and BMP are used simultaneously, rather than singly (FIG. 2A).

Upon inducing the differentiation into mesodermal cells, any known substance that facilitates the differentiation of embryonic stem cells into mesodermal cells and general media supplements may be further included, in addition to the MEK/ERK signal transduction inhibitor and BMP. Step 2) is generally performed for a time period sufficient to form the differentiated cells, preferably 3 to 5 days.

Step 3) is a step for inducing the differentiation into hemangioblasts by culturing the differentiated mesodermal cells in the presence of VEGF and bFGF. VEGF and bFGF are preferably contained in the medium at a concentration of 50 ng/ml, and any known substance that facilitates the differentiation into hemangioblasts and general media supplements may be further added thereto. Step 3) is generally performed for a time period sufficient to form the differentiated cells, preferably 3 to 5 days.

Step 4) is a step for inducing the differentiation of hemangioblasts into vascular endothelial cells, vascular smooth muscle cells, and hematopoietic stem cells under the suitable culture conditions. In order to differentiate hemangioblasts into vascular endothelial cells, hemangioblasts are preferably cultured for 3 to 5 days in the presence of VEGF and bFGF that are contained in the culture medium at a concentration of 50 ng/ml. Further, in order to differentiate hemangioblasts into vascular smooth muscle cells, hemangioblasts are preferably cultured for 3 to 5 days in the presence of PDGF-BB (Platelet-derived growth factor-BB) that are contained in the culture medium at a concentration of 50 ng/ml. Further, in order to differentiate hemangioblasts into hematopoietic stem cells, hemangioblasts are preferably cultured in MethCult GF H4434 (Stem Cell Technologies, Canada) for 15 days.

In examples of the present invention, the differentiation of human embryonic stem cells was induced according to the above 4 steps (FIG. 1). In step 1, human embryonic stem cells were co-cultured on the feeder cell, STO cell line. Then, for feeder-free culture, one colony was cut in a diameter of 300 to 500 μm using a needle of 10 ml syringe, and put on Matrigel, followed by culturing for 2 days in a conditioned medium supplemented with 4-8 ng/ml of bFGF. In step 2, the human embryonic stem cells that were cultured in the conditioned medium for 2 days were cultured for 3 days in an unconditioned medium that was supplemented with the MEK1/2 inhibitors, PD98059 and BMP-4 at a concentration of 20~50 μM and 10~20 ng/ml, respectively. At this time, the "unconditioned medium" means a bFGF-free culture medium for embryonic stem cells. In step 3, the cells were cultured for 3 days in an unconditioned medium that was supplemented with VEGF and bFGF at a concentration of 50 ng/ml, respectively. In step 4, cells expressing CD34 that is the hemangioblast-specific marker were separated using a microbead, so as to obtain only CD34 positive cells. The obtained CD34 positive cells were cultured for about 5 days in EGM (Endothelial cell Growth Medium, clonetics, USA) supplemented with VEGF and bFGF in order to differentiate into vascular endothelial cells. Further, the obtained CD34 positive cells were cultured for about 5 days in EGM (Endothelial cell Growth Medium, clonetics, USA) supplemented with 50 ng/ml of PDGF-BB in order to differentiate into vascular smooth muscle cells. Furthermore, the obtained CD34 positive cells were cultured for about 15 days in MethCult GF H4434 (Stem Cell Technologies, Canada) in order to differentiate into hematopoietic stem cells. The experiments were performed in accordance with the manufacturer's protocol.

The cells that are differentiated from embryonic stem cells by the method according to some embodiments of the present invention have morphological, physiological, or immunological features, preferably an increase in expression level of marker genes being specific to the differentiated cells. The hESC-derived mesodermal cells have a characteristic, for example, an increase in gene expression level of one or more mesoderm-specific markers from Goosecoid, Brachyury, TBX-4, TBX-5 and TBX-6. Further, the mesoderm-derived hemangioblasts are characterized in that they are CD34 positive. Further, the hemangioblast-derived vascular endothelial cells have a characteristic, for example, an increase in gene expression level of one or more vascular endothelial cell-specific markers from vWF (von Willerbrand factor), EphB4 (Ephrin receptor B4), VE-cadherin (Vascular Endothelial-cadherin), CD105 (endoglin) and CD31 (PECAM-1). Furthermore, the hemangioblasts-derived vascular smooth muscle cells have a characteristic, for example, an increase in gene expression level of one or more vascular smooth muscle cell-specific markers from SM22α, SM-MHC (smooth muscle-myosin heavy chain), PDGF-B receptor, α-SMA (α-smooth muscle actin), and calponin.

Figure 2:
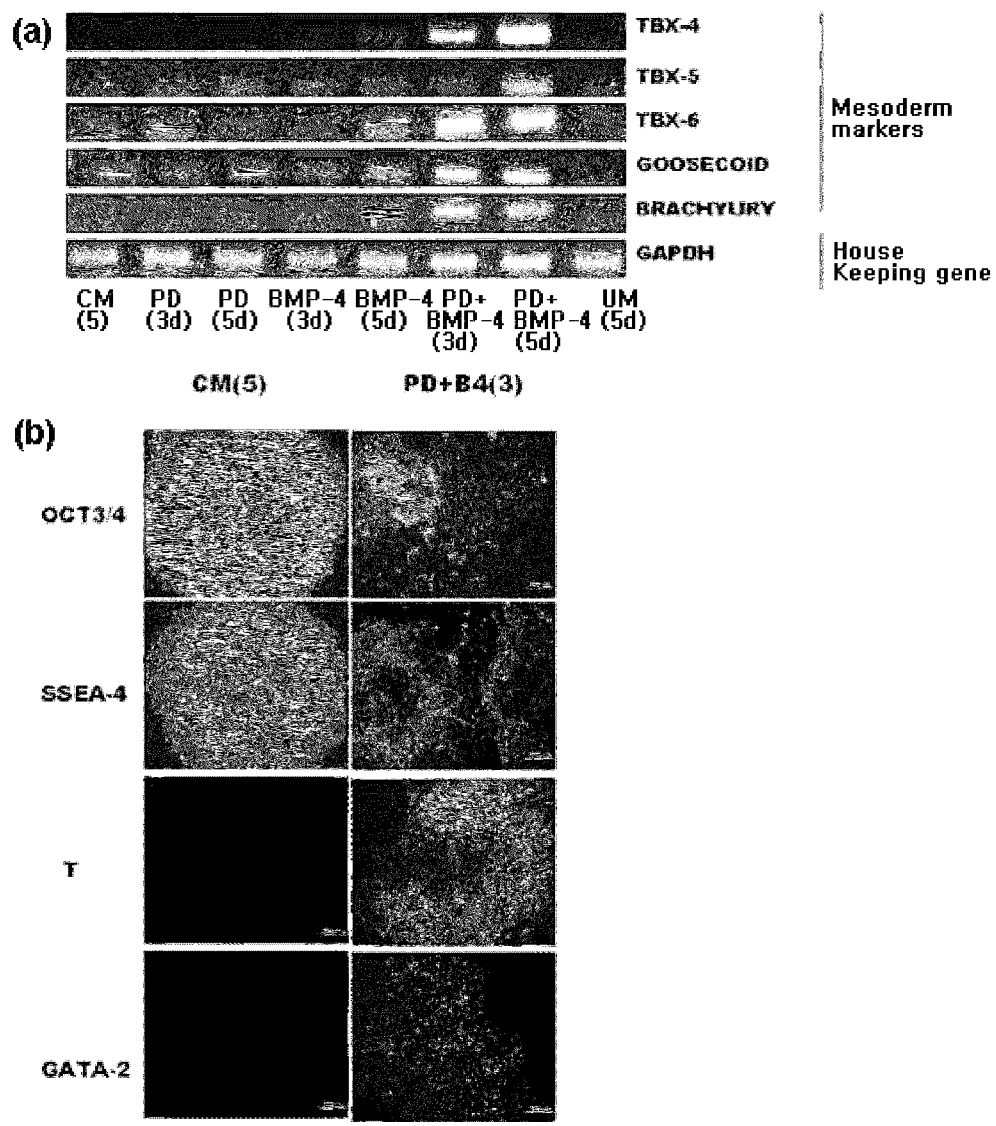
FIG. 2 shows the results of RT-PCR (a) and immunofluorescent staining (b), in which expressions of the mesoderm-specific marker genes were examined to confirm the differentiation of human embryonic stem cells into mesodermal cells.
Figure 3:
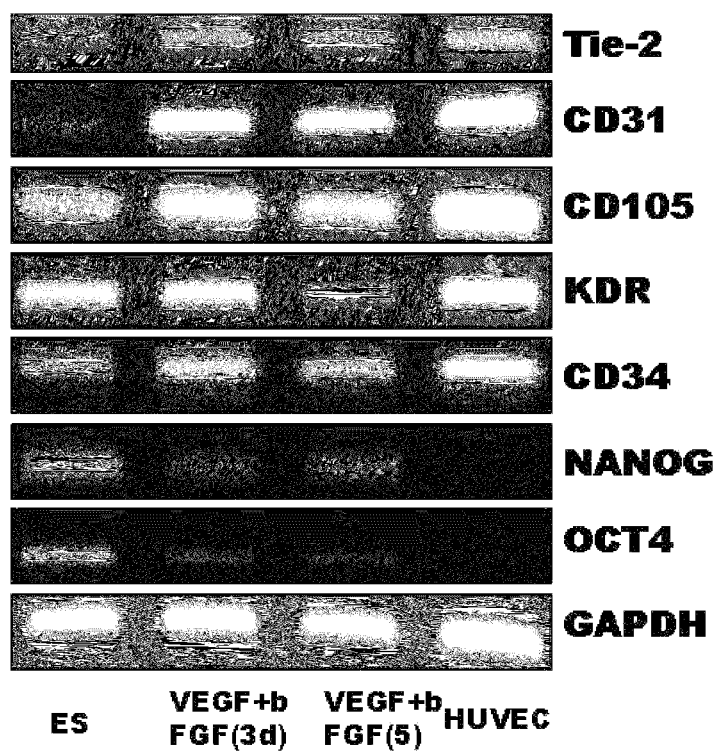
FIG. 3 shows the results of RT-PCR, in which expressions of the endothelial cell-specific markers (Tie-2, CD31, CD105 and KDR), the embryonic stem cell-specific markers (NANOG and OCT4), and the hemangioblast-specific marker (CD34) were examined to confirm the differentiation of hESC-derived mesodermal cells into hemangioblasts.
Figure 4:
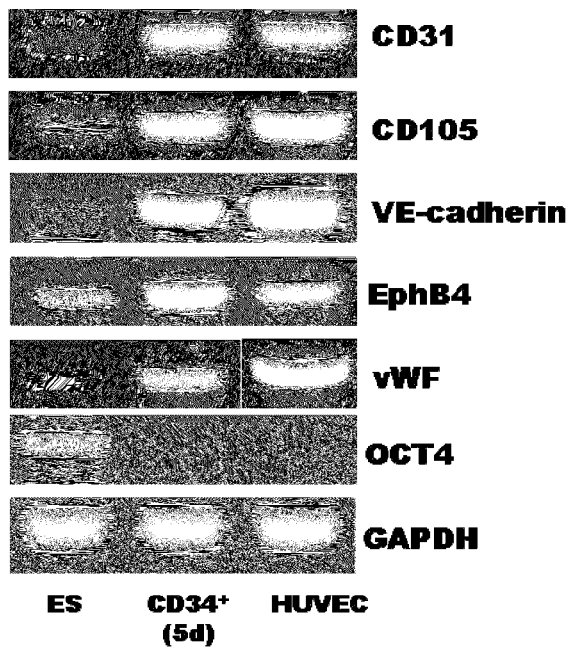
FIG. 4 shows the results of RT-PCR (a) and immunofluorescent staining (b-d), in which expressions of the vascular endothelial cell-specific markers (vWF, EphB4, VE-cadherin, CD105, and CD31) were examined to confirm the differentiation of hESC-derived hemangioblasts into vesicular endothelial cells. In addition, AcLDL uptake by the hESC-derived vascular endothelial cells was examined under a fluorescence microscope (e), morphology of the hESC-derived vascular endothelial cells was found to be similar to the pebble-like shape of mature vascular endothelial cells under a phase-contrast microscope (f), and the hESC-derived vascular endothelial cells were found to form cord-like structures, when they were cultured on Matrigel for 24 hrs (g).
Figure 4:
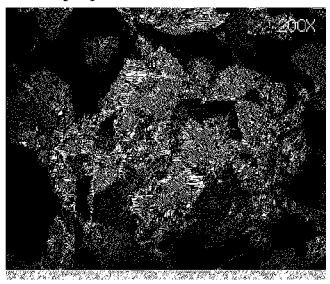
Figure 4:
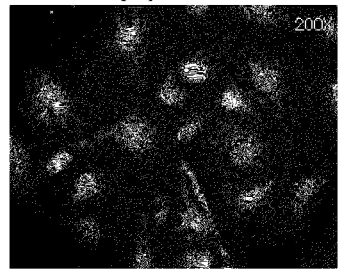
Figure 4:
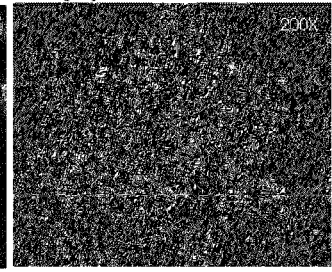
Figure 4:
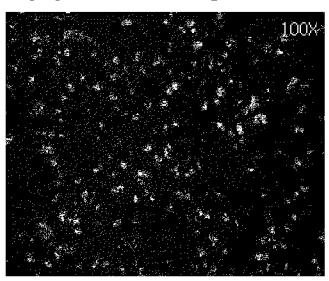
Figure 4:
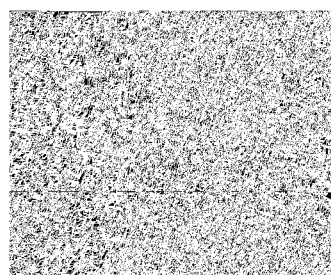
Figure 4:
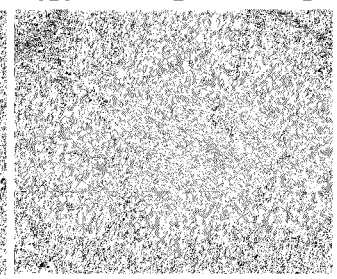
Figure 5:
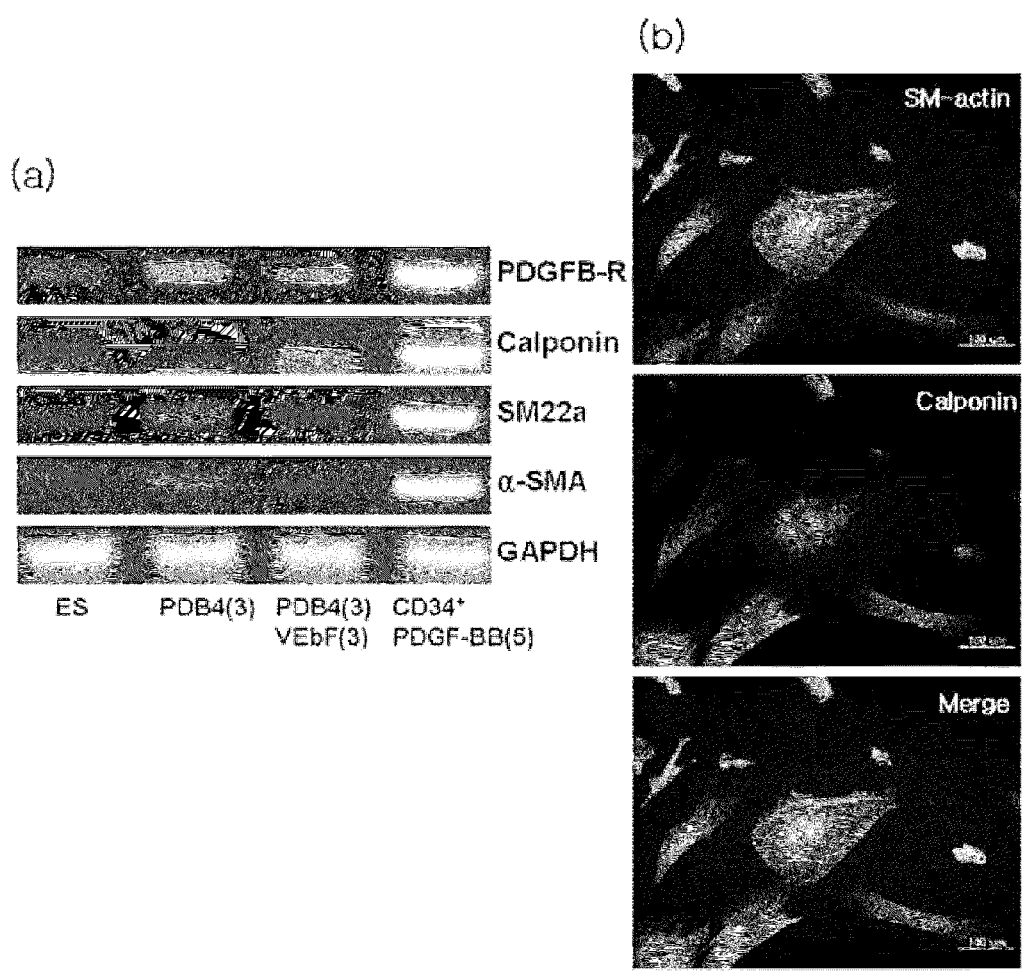
FIG. 5 shows the results of RT-PCR (a) and immunofluorescent staining (b), in which expressions of the vascular smooth muscle cell-specific markers were examined to confirm the differentiation of hESC-derived hemangioblasts into vascular smooth muscle cells.

In examples of the present invention, in order to confirm differentiation-inducing effects of the composition and the differentiation method using the same, human embryonic stem cells were treated with the MEK/ERK signal transduction inhibitor and BMP according to some embodiments of the present invention, and expression levels of the mesoderm-specific marker genes, Goosecoid, Brachyury, TBX-4, TBX-5, and TBX-6 were measured by RT-PCR and immunofluorescent staining (FIG. 2). The differentiated mesodermal cells were treated with VEGF and bFGF, and then expression level of the hemangioblast-specific marker, CD34 was measured by RT-PCR (FIG. 3). In addition, in order to confirm the differentiation of the hemangioblasts into vascular endothelial cells (FIG. 4), vascular smooth muscle cells (FIG. 5), or hematopoietic stem cells (FIG. 6), expression of the specific marker being specific to each cell was measured by RT-PCR. As a result, the composition according to some embodiments of the present invention was found to exhibit excellent differentiation-inducing effects.

Hereinafter, some embodiments of the present invention will be described in more detail with reference to Examples. However, these Examples are for the illustrative purpose only, and the invention is not intended to be limited by these Examples.

Example 1

Culture of Human Embryonic Stem Cells

In some examples of the present invention, human embryonic stem cells were cultured in DMEM/F12 (Invitrogen, USA) containing 20% knockout serum replacement (Invitrogen, USA), 0.1 mM non-essential amino acid (NEAA; Invitrogen, USA), 0.1 mM beta-mercaptoethanol, 4 ng/ml recombinant human basic FGF (Invitrogen, USA), and 1× penicillin-streptomycin (Invitrogen, USA), and then filtered using a 0.22 mm filter.

The human embryonic stem cells were co-cultured on feeder cells (STO cell line). For feeder-free culture, one colony was cut in a diameter of 300 to 500 μm using a needle of 10 ml syringe, and put on Matrigel, followed by culturing for 2 days in a conditioned medium supplemented with 4-8 ng/ml of bFGF.

Example 2

Induction of Differentiation of Human Embryonic Stem Cells into Mesodermal Cells 2-1. RT-PCR Analysis The human embryonic stem cells cultured in Example 1 were cultured for 3 days in a conditioned medium that contained the MEK1/2 inhibitors, PD98059 and BMP-4 at a concentration of 20~50 μM and 10~20 ng/ml, respectively. Then, in order to confirm the differentiation of human embryonic stem cells into mesodermal cells, expression of the mesoderm-specific marker genes was examined by RT-PCR. For analysis of gene expression, total RNA was isolated from cells, and cDNA was synthesized using reverse transcriptase, followed by PCR (polymerase-chain reaction) using primers specific to each gene.

As a control group, sample was cultured only in the conditioned medium for 5 days. As experimental groups, cells were cultured for 3 days and 5 days in culture media that were prepared by adding each of PD98059 and BMP-4 to the unconditioned medium at a concentration of 20~50 μM and 10~20 ng/ml, respectively. In addition, cells were simultaneously treated with PD98059 and BMP-4, and examined for 3 days and 5 days.

As shown in FIG. 2(A), expressions of the mesoderm-specific markers including BRACHYURY, GOOSECOID, TBX-4, TBX-5, and TBX-6 were observed in the sample that was treated with PD98059 and BMP-4, simultaneously. Expressions of the mesoderm-specific markers were not observed in the sample that was treated with PD98059 or BMP-4, singly.

2-2. Immunofluorescent Staining Analysis

In order to confirm the differentiation into mesodermal cells at protein level, expressions of the embryonic stem cell-specific markers and mesoderm-specific markers were examined by immunofluorescent staining in a sample that was only cultured and examined in the conditioned medium for 5 days and a sample that was treated with both PD98059 and BMP-4. In order to stain the hESC-derived mesodermal cells with the mesoderm-specific markers, BRACHYURY and GATA-2, the sample treated with PD98059 and BMP-4 for 3 days was first fixed in 4% paraformaldehyde at room temperature for 20 min, and then washed with a PBST solution (0.1% Tween-20 in PBS) for 5 min three times. To allow permeabilization of antibodies into the nucleus, a permeating solution (0.1% Triton X-100 in PBS) was added to culture plates, and left at room temperature for 15 min. After 15 min, the permeating solution was removed, and 4% FBS (Fetal Bovine Serum) was added for blocking at room temperature for 1 hr. Thereafter, Goat anti-human OCT4, Mouse anti-human SSEA-4 antibodies were diluted 1:300 in blocking buffer, and Goat anti-human BRACHYURY, Goat anti-human GATA-2 antibodies were diluted 1:100 in blocking buffer, and added to the culture plates, which were left at 4° C. for one day. Next day, in order to examine expressions of the markers (OCT4, SSEA-4, BRACHYURY, GATA-2) under a fluorescence microscope, secondary antibodies against the marker antibodies (Alexa 488 and Alexa 594-conjugated Donkey anti-goat IgG, Alexa 488-conjugated Goat anti-mouse IgG) were added, and left at room temperature for 1 hr. After 1 hr, the culture plates were washed with the PBST solution for 10 min five times, and a fluorescence microscope was used to examine their expressions.

As shown in FIG. 2(B), expression levels of the embryonic stem cell-specific markers, OCT3/4 and SSEA-4 were reduced depending on the treatment of PD98059 and BMP-4, and expressions of the mesoderm-specific markers, BRACHYURY and GATA-2 were observed.

Example 3

Induction of Differentiation of hESC-Derived Mesodermal Cells into Hemangioblasts The mesodermal cells obtained in Example 2 were cultured in an unconditioned medium containing VEGF and bFGF at each concentration of 50 ng/ml for 3 days, and expressions of the endothelial cell-specific markers (Tie-2, CD31, CD105 and KDR), the embryonic stem cell-specific markers (NANOG and OCT4), and the hemangioblast-specific marker (CD34) were examined by RT-PCR. For analysis of gene expression, total RNA was isolated from cells, and cDNA was synthesized using reverse transcriptase, followed by PCR (polymerase-chain reaction) using primers specific to each gene.

As shown in FIG. 3, in each sample treated with both VEGF and bFGF for 3 days and 5 days, expressions of the embryonic stem cell-specific markers (NANOG and OCT4) were not observed, but expression levels of the endothelial cell-specific markers (Tie-2, CD31, CD105 and KDR) and the hemangioblast-specific marker were increased. In this experiment, HUVEC was used as a positive control, which represents expression levels of the endothelial cell-specific markers and the hemangioblast-specific marker in the samples treated with VEGF and bFGF.

Example 4

Isolation of hESC-Derived Hemangioblasts and Differentiation into Vascular Endothelial Cells 4-1. RT-PCR Analysis Cells expressing CD34 that is the hemangioblast-specific marker were separated using a CD34 microbead, so as to obtain only CD34 positive cells. The obtained CD34 positive cells were cultured for about 5 days in EGM (Endothelial cell Growth Medium, clonetics, USA) containing VEGF and bFGF at each concentration of 50 ng/ml in order to differentiate into vascular endothelial cells. Expressions of the vascular endothelial cell-specific markers were examined by RT-PCR. For analysis of gene expression, total RNA was isolated from cells, and cDNA was synthesized using reverse transcriptase, followed by PCR (polymerase-chain reaction) using primers specific to each gene.

As shown in FIG. 4(a), when CD34 positive cells were cultured in EGM containing VEGF and bFGF, expression levels of the vascular endothelial cell-specific markers, vWF (von Willerbrand factor), EphB4 (Ephrin receptor B4), VE-cadherin (Vascular Endothelial-cadherin), CD105 (endoglin), and CD31 (PECAM-1) were similar to that of the positive control, HUVEC.

4-2. Immunofluorescent Staining Analysis

In order to confirm the differentiation into vascular endothelial cells at protein level, expressions of the vascular endothelial cell-specific markers were examined by immunofluorescent staining. In order to stain the hESC-derived vascular endothelial cells with the vascular endothelial cell-specific markers, PECAM-1, vWF, and VE-cadherin, the sample was first fixed in 4% paraformaldehyde at room temperature for 20 min, and then washed with a PBST solution (0.1% Tween-20 in PBS) for 5 min three times. To allow permeabilization of antibodies into the nucleus, a permeating solution (0.1% Triton X-100 in PBS) was added to culture plates, and left at room temperature for 15 min. After 15 min, the permeating solution was removed, and 4% NGS (Normal Goat Serum) was added for blocking at room temperature for 1 hr. Thereafter, mouse anti-human PECAM-1, Rabbit anti-human vWF, mouse anti-human VE-cadherin antibodies were diluted 1:100 in blocking buffer, and added to the culture plates, which were left at 4° C. for one day. Next day, in order to examine expressions of the markers (PECAM-1, vWF, VE-cadherin) under a fluorescence microscope, secondary antibodies against the marker antibodies (Alexa 488 and Alexa 594-conjugated Goat anti-mouse IgG, Alexa 488-conjugated Goat anti-Rabbit poly) were added, and left at room temperature for 1 hr. After 1 hr, the culture plates were washed with a PBST solution for 10 min five times, and a fluorescence microscope was used to examine their expressions.

As shown in FIGS. 4(b)-(d), expressions of the vascular endothelial cell-specific markers, vWF, VE-cadherin, and CD31 (PECAM-1) were observed.

4-3. Examination of AcLDL Uptake, Morphology, and Cord-Like Structure Formation

Mature endothelial cells have a property of LDL (Low Density Lipoprotein) uptake, which was examined in the hESC-derived vascular endothelial cells. AcLDL (acetylated LDL) was added to the culture medium for about 4 hrs, and then a fluorescence microscope was used to confirm AcLDL uptake by the hESC-derived vascular endothelial cells (FIG. 4(e)).

Further, morphology of the hESC-derived vascular endothelial cells was found to be similar to the pebble-like shape of mature vascular endothelial cells, examined with a phase-contrast microscope (FIG. 4(f)).

Furthermore, when vascular endothelial cells are cultured on Matrigel, they form cord-like structures. In order to confirm whether the hESC-derived vascular endothelial cells also had the property, the hESC-derived vascular endothelial cells were cultured on Matrigel for 24 hrs. As a result, it was found that they formed cord-like structures (FIG. 4(g)).

Example 5

Differentiation of hESC-Derived Hemangioblasts into Vascular Smooth Muscle Cells 5-1. RT-PCR Analysis In order to differentiate CD34 positive cells into vascular smooth muscle cells, CD34 positive cells were cultured for about 5 days in EGM (Endothelial cell Growth Medium, clonetics, USA) containing PDGF-BB at a concentration of 50 ng/ml. Expressions of the vascular smooth muscle cell-specific markers were examined by RT-PCR. For analysis of gene expression, total RNA was isolated from cells, and cDNA was synthesized using reverse transcriptase, followed by PCR (polymerase-chain reaction) using primers specific to each gene.

As shown in FIG. 5(a), the CD34 positive cells were found to express the vascular smooth muscle cell-specific markers, SM22α, SM-MHC (smooth muscle-myosin heavy chain), PDGF-B receptor, α-SMA (α-smooth muscle actin), and calponin in EGM-2 culture medium containing PDGF-BB.

5-2. Immunofluorescent Staining Analysis

In order to confirm the differentiation into vascular smooth muscle cell at protein level, expressions of the vascular smooth muscle cell-specific markers were examined by immunofluorescent staining. In order to stain the hESC-derived vascular smooth muscle cells with the vascular smooth muscle cell-specific markers, α-smooth muscle actin (α-SMA) and calponin, the sample was first fixed in 4% paraformaldehyde at room temperature for 20 min, and then washed with a PBST solution (0.1% Tween-20 in PBS) for 5 min three times. To allow permeabilization of antibodies into the nucleus, a permeating solution (0.1% Triton X-100 in PBS) was added to culture plates, and left at room temperature for 15 min. After 15 min, the permeating solution was removed, and 4% NGS (Normal Goat Serum) was added for blocking at room temperature for 1 hr. Thereafter, mouse anti-human α-SMA, Rabbit anti-human calponin antibodies were diluted 1:100 in blocking buffer, and added to the culture plates, which were left at 4° C. for one day. Next day, in order to examine expressions of the markers (α-SMA, calponin) under a fluorescence microscope, secondary antibodies against the marker antibodies (Alexa 488-conjugated Goat anti-mouse IgG and Alexa 594-conjugated Goat anti-Rabbit poly) were added, and left at room temperature for 1 hr. After 1 hr, the culture plates were washed with a PBST solution for 10 min five times, and a fluorescence microscope was used to examine their expressions.

As shown in FIG. 5(b), expressions of the vascular smooth muscle cell-specific markers, α-SMA and calponin were also observed at protein level.

Example 6

Differentiation of hESC-Derived Hemangioblasts into Hematopoietic Stem Cells

In order to differentiate CD34 positive cells into hematopoietic stem cells, CD34 positive cells were cultured for about 15 days in MethCult GFH4434 (Stem Cell Technologies, Canada). The experiments were performed in accordance with the manufacturer's protocol. In order to confirm the differentiation of CD34 positive cells into hematopoietic stem cells, CFU (colony forming unit) assay was performed. In order to perform CFU assay, the CD34 positive cells were first washed with IMDM (Iscove's MDM), and then serially diluted (500, 1000, 5000, $5\times10^4$, $1\times10^5$ cells, etc.). The diluted cells were added to semi-solid media made of methylcellulose polymer, manufactured by StemCell Technology. Components that were added to the media are as follows.

Iscove's MDM
1% Methylcellulose
30% Fetal Bovine serum
1% Bovine Serum Albumin
$10^{-4}$ M 2-Merchaptoethanol
2 mM L-glutamine
50 ng/ml Stem Cell Factor
10 ng/ml GM-CSF
10 ng/ml IL-3
3 U/ml Erythropoietin The CD34 positive cells were cultured in the media at 37° C. and 5% $CO_2$ for 14 to 20 days, and cell shape and the number of colonies were examined for characterization of each colony.

Figure 6:
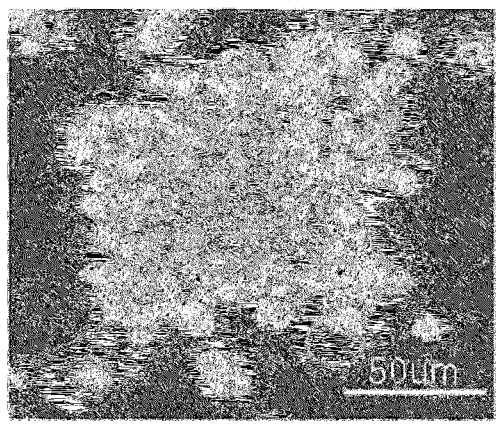
FIG. 6 shows the results of CFU (colony forming unit) assay, in which generation of macrophage, erythrocyte and granulocyte was examined to confirm the differentiation of hESC-derived hemangioblasts into hematopoietic stem cells.
Figure 6:
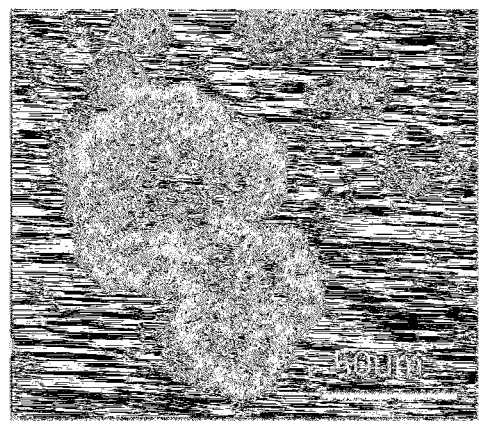
Figure 6:
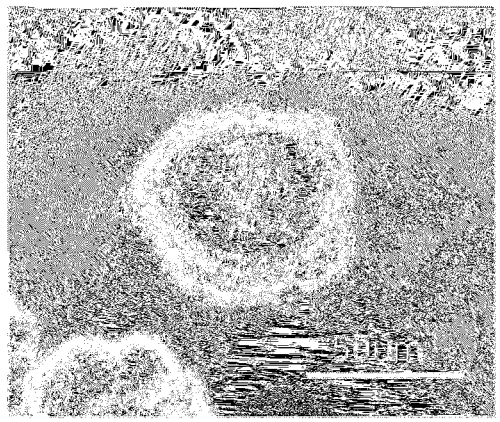
Figure 6:
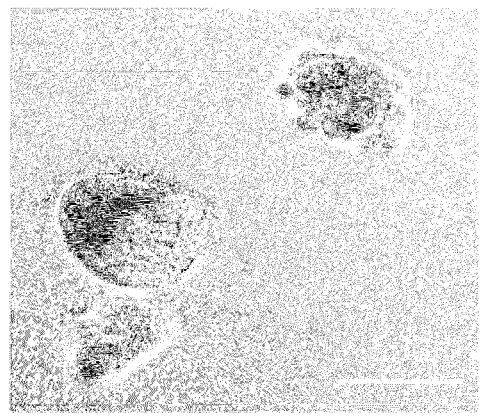

As shown in FIG. 6, it was found that blood cells such as macrophage, erythrocyte and granulocyte were generated from CD34 positive cells, indicating that the CD34 positive cells differentiated by the present inventors were differentiated into hematopoietic stem cells.

As mentioned above, the MEK/ERK signal transduction inhibitor and BMP can be used to regulate the signaling pathway in human embryonic stem cells for differentiation into mesodermal cells. Treatment of the differentiated mesodermal cells with VEGF and bFGF effectively induces their differentiation into hemangioblasts, which further differentiate into vascular endothelial cells, vascular smooth muscle cells, and hematopoietic stem cells, without any addition of animal serum. Such method is able to induce the differentiation of embryonic stem cells into a variety of cells, and contribute to research on early human development.

What is claimed is:

1. A method for inducing differentiation of human embryonic stem cells into mesodermal cells, the method comprising the step of:
    culturing human embryonic stem cells in a cell culture medium comprising:
    a MEK/ERK (mitogen-activated protein kinase/extracellular regulated kinase) signal transduction inhibitor, wherein the MEK/ERK signal transduction inhibitor is PD98059 or U0126; and
    bone morphogenic protein 4 (BMP4), whereby the human embryonic stem cells differentiate into mesodermal cells.

2. The method according to claim 1, wherein a concentration of the MEK/ERK signal transduction inhibitor is 20 to 50 μM.

3. The method according to claim 1, wherein a concentration of BMP4 is 10 to 20 μM.

4. The method according to claim 1, wherein the cells are cultured in the culture medium for 3 to 5 days.

5. A method for inducing differentiation of human embryonic stem cells into hemangioblasts, the method comprising the steps of:
    i) culturing the human embryonic stem cells in a cell culture medium comprising:
        a MEK/ERK (mitogen-activated protein kinase/extracellular regulated kinase) signal transduction inhibitor, wherein the MEK/ERK final transduction inhibitor is PD98059 or U0126; and
        BMP4,
    whereby the human embryonic stem cells differentiate into mesodermal cells; and
    ii) culturing the differentiated mesodermal cells in a cell culture medium comprising:
        VEGF (vascular endothelial cell growth factor); and
        bFGF (basic fibroblast growth factor),
    whereby the differentiated mesodermal cells differentiate into hemangioblasts.

6. The method according to claim 5, wherein each concentration of VEGF and bFGF is 50 ng/ml.

7. The method according to claim 5, wherein the cells are cultured in the culture medium of step ii) for 3 to 5 days.

* * * * *